United States Patent [19]
Kushnerick et al.

[11] Patent Number: 4,831,204
[45] Date of Patent: * May 16, 1989

[54] PRODUCTION OF GASOLINE FROM LIGHT OLEFINS WITH FCC GAS PLANT IMPROVEMENT BY OLEFIN UPGRADING

[75] Inventors: John D. Kushnerick, Boothwyn, Pa.; Samuel A. Tabak, Wenonah, N.J.

[73] Assignee: Mobile Oil Corporation, New York, N.Y.

[ * ] Notice: The portion of the term of this patent subsequent to May 16, 2006 has been disclaimed.

[21] Appl. No.: 133,772

[22] Filed: Dec. 16, 1987

[51] Int. Cl.⁴ .............................................. C07C 2/12
[52] U.S. Cl. .................................... 585/519; 585/533; 422/131; 422/190
[58] Field of Search ................ 585/519, 522; 422/190, 422/131

[56] References Cited

U.S. PATENT DOCUMENTS

| | | | |
|---|---|---|---|
| 4,471,147 | 9/1984 | Owen et al. | 585/519 |
| 4,504,691 | 3/1985 | Hsia et al. | 585/519 |
| 4,511,747 | 4/1985 | Wright et al. | 585/415 |

FOREIGN PATENT DOCUMENTS 0113180  7/1984  European Pat. Off. ............ 585/519

Primary Examiner—Asok Pal
Attorney, Agent, or Firm—Alexander J. McKillop; Charles J. Speciale; L. G. Wise

[57] ABSTRACT

A continuous technique for upgrading light olefinic crackate gas from hydrocarbon cracking comprising methods and means for: (a) compressing and cooling a first portion of the light crackate gas to provide a first pressurized ethene-rich vapor stream and a first condensed crackate stream rich in $C_3+$ aliphatics; (b) contacting said first ethene-rich vapor stream under pressure with a $C_5+$ liquid sorbent stream in a gas-liquid contact absorber column under sorption conditions to selectively absorb a major amount of $C_3+$ components; (c) recovering a second ethene-rich vapor stream overhead from the absorber column; (d) converting said second ethene-rich vapor stream in a reaction zone in once-through contact with a fluidized bed of said medium pore zeolite catalyst solid particles under oligomerization conditions to produce an olefinic hydrocarbon effluent stream rich in $C_5+$ hydrocarbons; (e) cooling and separating the reaction effluent stream to provide a light offgas stream and a condensed liquid hydrocarbon product stream; (f) fractionating the condensed liquid hydrocarbon product stream in the absorber column concurrently with sorption of the first ethene-rich vapor stream for recovery of liquid hydrocarbon product with an absorber bottoms liquid stream rich in $C_3+$ components; (g) further fractionating the absorber bottoms liquid stream to provide a $C_3-C_4$ product and a liquid hydrocarbon fraction consisting essentially of $C_5+$ hydrocarbons; (h) recycling at least a portion of the $C_5+$ liquid hydrocarbon fraction to the absorber column as the liquid sorbent stream; and bypassing a second portion of said light crackate gas around said absorber to the reaction zone for conversion concurrently with said second ethene-rich vapor stream.

3 Claims, 2 Drawing Sheets

PRODUCTION OF GASOLINE FROM LIGHT OLEFINS WITH FCC GAS PLANT IMPROVEMENT BY OLEFIN UPGRADING

FIELD OF THE INVENTION

This invention relates to an improved technique for integrating an olefins upgrading process for the catalytic conversion of olefinic feedstocks to liquid hydrocarbons boiling in the gasoline and fuel oil range with the processing and separation of light cracking gases. In particular, it provides an improved reactor system and hydrocarbon separation technique for debottlenecking fluid catalyst cracking production units.

BACKGROUND OF THE INVENTION

Hydrocarbon mixtures containing significant quantities of light olefins are frequently encountered in petrochemical plants and petroleum refineries. Because of the ease with which olefins react, these streams serve as feedstocks in a variety of hydrocarbon conversion processes. Many olefinic conversion processes require that the olefinic feed be provided in a highly purified condition. However, processes which may utilize the olefinic feedstocks without the need for further separation and purification are highly desirable.

Although the main purpose of fluidized catalytic cracking (FCC) is to convert gas oils to compounds of lower molecular weight in the gasoline and middle distillate boiling ranges, significant quantities of $C_1$–$C_4$ hydrocarbons are also produced. These light hydrocarbon gases are rich in olefins which heretofore have made them prime candidates for conversion to gasoline blending stocks by means of polymerization and/or alkylation. Fractionation of the effluent from the fluid catalytic cracking reactor has been employed to effect an initial separation of this stream. The gaseous overhead from the main fractionator is collected and processed in the FCC gas plant. Here the gases are compressed, contacted with a naphtha stream, scrubbed, where necessary, with an amine solution to remove sulfur and then fractionated to provide, for example, light olefins and isobutane for alkylation, light olefins for polymerization, n-butane for gasoline blending and propane for LPG. Light gases are recovered for use as fuel.

Since alkylation units were more costly to build and operate than polymerization units, olefin polymerization was initially favored as the route for providing blending stocks. Increased gasoline demand and rising octane requirements soon favored the use of alkylation because it provided gasoline blending stocks at a higher yield and with a higher octane rating than the comparable polymerized product. However, catalytic alkylation can present some safety and disposal problems. In addition, feedstock purification is often required to prevent catalyst contamination. Further, sometimes there is insufficient isobutane available in a refinery to permit all the olefins from the FCC to be catalytically alkylated.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of ZSM-5 or related zeolite. In U.S. Pat. Nos. 4,150,062 and 4,227,992 Garwood et al disclose the operating conditions for the Mobil Olefin to Gasoline/Distillate (MOGD) process for selective conversion of $C_3+$ olefins. A fluidized bed process for converting ethene-containing light olefinic streams, sometimes referred to as the Mobil Olefins to Gasoline (MOG) process is described by Avidan et al in U.S. patent application No. 006,407, filed Jan 23, 1987. The phenomena of shape-selective polymerization are discussed by Garwood in ACS Symposium Series No. 218, Intrazeolite Chemistry, "Conversion of $C_2$–$C_{10}$ to Higher Olefins over Synthetic Zeolite ZSM-5", 1983 American Chemical Society.

In the process for catalytic conversion of olefins to heavier hydrocarbons by catalytic oligomerization using an acid crystalline metallosilicate zeolite, such as ZSM-5 or related shape-selective catalyst, process conditions can be varied to favor the formation of either gasoline or distillate range products. In the gasoline operating mode, or MOG reactor system, ethylene and the other lower olefins are catalytically oligomerized at elevated temperature and moderate pressure. Under these conditions ethylene conversion rate is greatly increased and lower olefin oligomerization is nearly complete to produce an olefinic gasoline comprising hexene, heptene, octene and other $C_6+$ hydrocarbons in good yield.

The olefins contained in an FCC gas plant would be an advantageous feed for MOG. U.S. Pat. No. 4,090,949 discloses upgrading olefinic gasoline by conversion thereof in the presence of carbon hydrogen-contributing fragments including olefins and a zeolite catalyst and where the contributing olefins may be obtained from a gas plant. U.S. Pat. Nos. 4,471,147 and 4,504,691 disclose an MOG/D process using an olefinic feedstock derived from FCC effluent. In these two latter patents the first step involves prefractionating the olefinic feedstock to obtain a gaseous stream rich in ethylene and a liquid stream containing $C_3+$ olefin. While the above patents disclose the general use of olefins obtained from FCC effluent as feedstocks for upgrading conversion, there is not a disclosure of integrating unit operations so as to improve both the oligomerization process and the processing of FCC effluent in a typical FCC gas plant.

Published European Patent Application No. 0,113,180 (Graven and McGovern) discloses such integration of olefins upgrading with a FCC plant. In this published application the olefin feedstock for MOGD comprises the discharge stream from the final stage of the wet gas compressor or the overhead from the high pressure receiver which separates the condensed effluent from the final stage wet gas compressor contained in the gas plant. The present invention improves upon such integrated process by incorporating olefins upgrading advantageously with the FCC gas plant.

SUMMARY OF THE INVENTION

This invention relates to an improvement in the process for upgrading light olefinic crackate gas from hydrocarbon cracking, said light crackate wet gas containing ethene, propene and other $C_1$–$C_4$ lower aliphatics, including a novel technique for debottlenecking an existing FCC plant to increase fuel production therein. A continuous reactor system is provided for upgrading light olefinic crackate gas from hydrocarbon cracking, said light crackate gas containing ethene propene and other $C_1$–$C_4$ lower aliphatics. This apparatus includes: (a) means for compressing and cooling the light crackate gas to provide a first pressurized ethene-rich vapor stream and a first condensed crackate stream rich in $C_3+$ aliphatics; (b) absorber means for contacting a first portion of said first ethene-rich vapor stream under pressure with a $C_5+$ liquid sorbent stream in a gas-liquid contact column under sorption conditions to selectively absorb a major amount of $C_3+$ components; (c) means for recovering a second ethene-rich vapor stream from the absorber column; (d) fluidized bed reactor means for converting said second ethene-rich vapor stream in once-through contact with a fluidized bed of acid medium pore zeolite catalyst solid particles under oligomerization conditions to produce an olefinic hydrocarbon effluent stream rich in $C_5+$ hydrocarbons; (e) means for cooling and separating the reaction effluent stream to provide a light offgas stream and a condensed liquid hydrocarbon product stream; (f) first fractionation means for fractionating the liquid hydrocarbon product stream in the absorber column concurrently with sorption of the first ethene-rich vapor stream for recovery of liquid hydrocarbon product with an absorber bottoms liquid stream rich in $C_3+$ components; (g) second fractionation means for further fractionating the absorber bottoms liquid stream to provide a $C_3$–$C_4$ product and a liquid hydrocarbon fraction consisting essentially of $C_5+$ hydrocarbons; (h) fluid handling means for recycling at least a portion of the $C_5+$ liquid hydrocarbon fraction to the absorber column as the liquid sorbent stream; and (i) means for passing a second portion of said first ethene-rich vapor stream to said reactor means (d) for conversion concurrently with said second ethene-rich vapor stream.

DETAILED DESCRIPTION OF THE INVENTION

Figure 1:
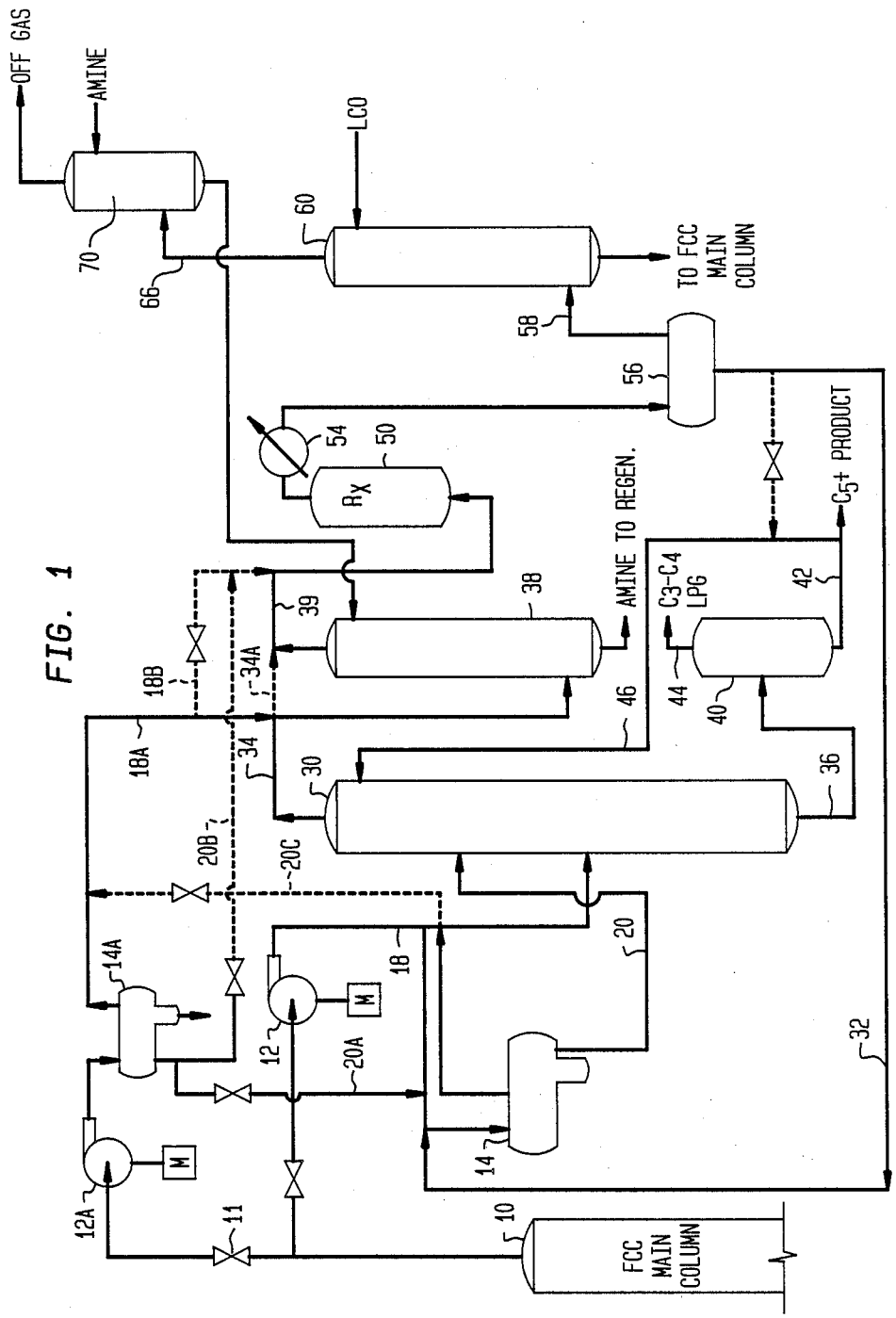
FIG. 1 is a schematic process diagram of a typical FCC gas plant with an integrated olefins upgrading unit for fuel gas conversion.

The present invention provides a system for upgrading FCC light olefins to liquid hydrocarbons, utilizing a continuous process for producing fuel products by oligomerizing olefinic components to produce olefinic product for use as fuel or the like. It provides a technique for oligomerizing lower alkene-containing light gas feedstock, optionally containing ethene, propene, butenes or lower alkanes, to produce predominantly $C_5+$ hydrocarbons, including olefins.

The preferred feedstock contains $C_2$–$C_4$ alkenes (mono-olefin) in the range of about 10 to 90 wt %. Non-deleterious components, such as methane and other paraffins and inert gases, may be present. A particularly useful feedstock is a light gas by-product of FCC gas oil cracking units containing typically 10–40 mol % $C_2$–$C_4$ olefins and 5–35 mol % $H_2$ with varying amounts of $C_1$–$C_3$ paraffins and inert gas, such as $N_2$. The process may be tolerant of a wide range of lower alkanes, from 0 to 95%. Preferred feedstocks contain more than 50 wt. % $C_1$–$C_4$ lower aliphatic hydrocarbons, and contain sufficient olefins to provide total olefinic partial pressure of at least 50 kPa. Under the reaction severity conditions employed in the present invention lower alkanes especially propane, may be partially converted to $C_4+$ products.

Conversion of lower olefins, especially ethene, propene and butenes, over HZSM-5 is effective at moderately elevated temperatures and pressures. The conversion products are sought as liquid fuels, especially the $C_5+$ hydrocarbons. Product distribution for liquid hydrocarbons can be varied by controlling process conditions, such as temperature, pressure and space velocity. Gasoline (e.g., $C_5$–$C_9$) is readily formed at elevated temperature (e.g., up to about 400° C.) and moderate pressure from ambient to about 5500 kPa, preferably about 250 to 2900 kPa. Under appropriate conditions of catalyst activity, reaction temperature and space velocity, predominantly olefinic gasoline can be produced in good yield and may be recovered as a product. Operating details for typical olefin oligomerization units are disclosed in U.S. Pat. Nos. 4,456,779; 4,497,968 (Owen et al.) and 4,433,185 (Tabak), incorporated herein by reference.

It has been found that $C_2$–$C_4$ rich olefinic light gas can be upgraded to liquid hydrocarbons rich in olefinic gasoline by catalytic conversion in a turbulent fluidized bed of solid acid zeolite catalyst under low severity reaction conditions in a single pass or with recycle of gaseous effluent components. This technique is particularly useful for upgrading LPG and FCC light gas, which usually contains significant amounts of ethene, propene, butenes, $C_2$–$C_4$ paraffins and hydrogen produced in cracking heavy petroleum oils or the like. It is a primary object of the present invention to provide a novel technique for upgrading such lower olefinic feedstock to distillate and gasoline range hydrocarbons in an economic multistage reactor system.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalyst preferred for use in olefins conversion includes the medium pore (i.e., about 5–7 angstroms) shape selective crystalline aluminosilicate zeolites having a silica to alumina ratio of about 20:1 or greater, a constraint index of about 1–12, and acid cracking activity (alpha value) of about 10–200. Representative of the shape selective zeolites are ZSM-5, ZSM-11, ZSM-12, ZSM-22, ZSM-23, ZSM-35 and ZSM-48. ZSM-5 is disclosed in U.S. Pat. No. 3,702,886 and U.S. Pat. No. Re. 29,948. Other suitable zeolites are disclosed in U.S. Pat. Nos. 3,709,979 (ZSM-11); 3,832,449 (ZSM-12); 4,076,979; 4,076,842 (ZSM-23); 4,016,245 (ZSM-35); and 4,375,573 (ZSM-48). The disclosures of these patents are incorporated herein by reference.

While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of aluminosilicate ZSM-5 zeolite with 5 to 95 wt. % silica, clay and/or alumina binder.

These siliceous zeolites may be employed in their acid forms ion exchanged or impregnated with one or more suitable metals, such as Ga, Pd, Zn, Ni, Co and/or other metals of Periodic Groups III to VIII. Ni-exchanged or impregnated catalyst is particularly useful in converting ethene under low severity conditions. The zeolite may include other components, generally one or more metals of group IB, IIB, IIIB, VA, VIA or VIIIA of the Periodic Table (IUPAC). Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g., ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone. Certain of the ZSM-5 type medium pore shape selective catalysts are sometimes known as pentasils. In addition to the preferred aluminosilicates, the borosilicate, ferrosilicate and "silicalite" materials may be employed.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred.

A further useful catalyst is a medium pore shape selective crystalline aluminosilicate zeolite as described above containing at least one Group VIII metal, for example Ni-ZSM-5. This catalyst has been shown to convert ethylene at moderate temperatures and is disclosed in a copending U.S. patent application Ser. No. 893,522, filed Aug. 4, 1986 by Garwood et al, incorporated herein by reference.

Process and Equipment Description

A typical system for integrating MOG into an FCC gas plant is shown in FIG. 1. The present invention contemplates integrating gasoline mode (MOG) olefin upgrading into a FCC gas plant. In this alternative, the MOG reactor is incorporated into the FCC gas plant for optimizing single pass conversion of FCC olefins.

Process integration can be adapted to employ certain features of an unsaturated gas plant (USGP), especially multistage compression, phase separation, distillation absorption and the operatively connected unit operations essential to recovery of light cracking products or similar aliphatic hydrocarbon streams. In one embodiment, an integrated fluidized bed reactor is maintained in steady state operation at appropriate feed rate, temperature, pressure and catalyst activity to effect the desired oligomerization of lower olefinic components in the feedstock to gasoline range hydrocarbons.

Figure 2:
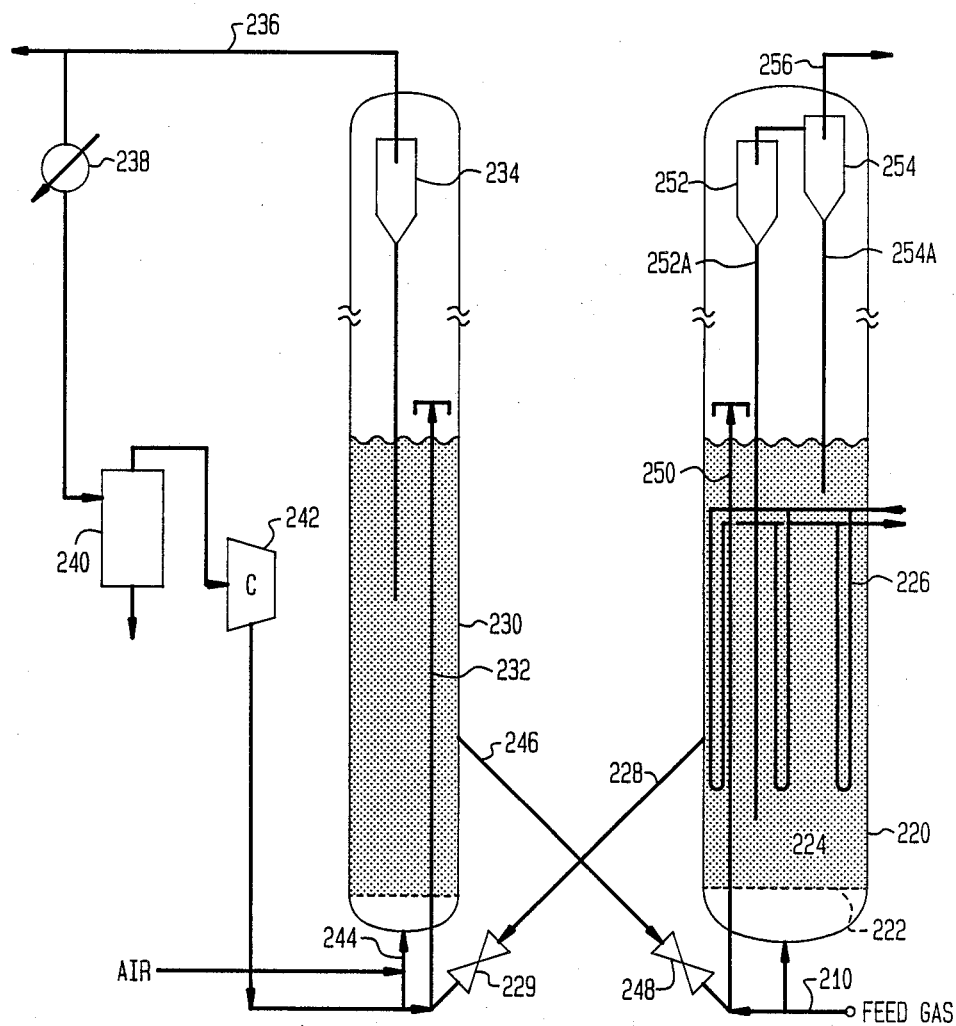
FIG. 2 is a vertical cross-section view of a preferred fluidized bed reactor system according to the present invention.

The embodiment depicted in FIG. 1 provides operating techniques and processing equipment for integrating the light FCC crackate recovery with olefins upgrading in a fluidized bed system. Interstage fractionation may be adapted to utilize conventional petroleum refinery cracking plant equipment in a novel process for upgrading light olefinic crackate gas from hydrocarbon cracking. The light crackate gas containing ethene propene and other $C_1$-$C_4$ lower aliphatics is passed from the FCC main column to means 12 for compressing the light crackate gas to provide a first pressurized ethene-rich vapor stream 18 and a first condensed crackate stream 20 rich in $C_3$+ aliphatics. Absorber tower 30 provides means for contacting the first ethene-rich vapor stream under pressure with a $C_5$+ liquid sorbent stream 46 in the absorber column under sorption conditions to selectively absorb a major amount of $C_3$+ components introduced via gas stream 18 and liquid stream 20, thus recovering a second ethene-rich vapor stream 34 from the absorber de-ethanaizer column. The $C_3$+ liquid bottoms stream 36 may be further fractionated in a debutanizer tower 40 to provide a $C_5$+ liquid gasoline product 42 and LPG product 44. Optionally, the pressurized FCC light gas stream may be contacted with amine in absorber tower 38 to remove any $H_2S$. The ethylenic gas is then upgraded in reactor means 50 by reacting the second ethene-rich vapor stream in once-through contact with a fluidized bed of acid medium pore zeolite catalyst particles under oligomerization conditions to produce an olefinic hydrocarbon effluent stream rich in $C_5$+ hydrocarbons. Preferably, this is a fluid bed reactor as depicted in FIG. 2 and described herein.

As part of the reactor effluent recovery system, means are provided for cooling and separating the reaction effluent stream to provide a light offgas stream and a condensed liquid hydrocarbon product stream. Advantageously, this is achieved by cooler means 54 and phase separator means 56. Recovery of a wild gasoline liquid stream 32 containing normally liquid components and volatile $C_3$-$C_4$ components permits recycle of this stream to provide for fractionating the liquid hydrocarbon product stream in the absorber column concurrently with sorption of the first ethene-rich vapor stream for recovery of liquid hydrocarbon product with the absorber bottoms liquid stream 36 rich in $C_3$+ components.

Absorber efficiency is enhanced by further fractionating the absorber bottoms liquid stream to provide a $C_3$-$C_4$ product and a liquid hydrocarbon fraction consisting essentially of $C_5$+ hydrocarbons, and recycling at least a portion of the $C_5$+ liquid hydrocarbon fraction via conduit 46 to the upper stages of absorber column 30 as the liquid sorbent stream.

The process is particularly useful for fractionating FCC gas oil crackate in an FCC main fractionation column in combination with sponge absorber 60. This is achieved by contacting light offgas stream 58 from accumulator 56 with a sponge oil in the secondary sponge absorber 60 to recover residual heavier hydrocarbons. When the sponge oil sorbent stream contains signficant amounts of $H_2S$ acid gas introduced with light cycle oil from refinery operations, it is desirable to remove this from overhead gas stream 62 in optional amine scrubber means 70, operatively connected to the prescrubber 38. This operation can be further integrated by passing sponge oil sorbate liquid from the secondary absorber to the FCC main fractionation column 10 for recovery. The above described integration technique is particularly useful where the condensed liquid hydrocarbon stream 32 contains volatile components and passes into the main absorber column 30 at an upper portion thereof to provide additional sorbent liquid.

The improvement herein is achieved advantageously by passing a second stream portion of light crackate gas from the FCC main column 10 around absorber 30 to reactor 50 for conversion concurrently with the primary ethene-rich vapor streams 34A and/or 39. The secondary FCC light gas bypass stream may be controlled by valve means 11, and passes through fluid handling compression means 12A and optional phase separator 14A from which is recovered a condensed liquid stream 20A. Optionally, liquid from separator 14A may be sent directly to reactor 50 via conduit 20B for combining with treated ethene-rich gas in reactor feed line 39. Compressed vapor from separator 14A may be combined via conduit 18A with stream 34. Other process options for bypassing the absorber operation are shown by lines 18B and 20C.

Fluidized Bed Reactor Operation

Referring to FIG. 2 of the drawing, a typical MOG type oligomerization reactor unit is depicted employing a temperature-controlled catalyst zone with indirect heat exchange and/or adjustable gas quench, whereby the reaction exotherm can be carefully controlled to prevent excessive temperature above the usual operating range of about 260° C. to 430° C., preferably at average reactor temperature of 300° C. to 400° C. Energy conservation in the system may utilize at least a portion of the reactor exotherm heat value by exchanging hot reactor effluent with feedstock and/or recycle streams. Optional heat exchangers may recover heat from the effluent stream prior to fractionation. Part of all of the reaction heat can be removed from the reactor without using the indirect heat exchange tubes by using cold feed, whereby reactor temperature can be controlled by adjusting feed temperature. The internal heat exchange tubes can still be used as internal baffles which lower reactor hydraulic diameter, and axial and radial mixing. The use of a fluid-bed reactor offers several advantages over a fixed-bed reactor. Due to continuous catalyst regeneration, fluid-bed reactor operation will not be adversely affected by oxygenate, sulfur and/or nitrogen containing contaminants presented in FCC light gas.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A. Accordingly, the fluidization regime is controlled to assure operation between the transition velocity and transport velocity. Fluidization operating conditions are described in detail in copending U.S. patent application Ser. No. 006,407, filed Jan. 23, 1987, incorporated herein by reference. Fluidization conditions are substantially different from those found in non-turbulent dense beds or transport beds.

The oligomerization reaction severity conditions can be controlled to optimize yield of $C_5$-$C_9$ aliphatic hydrocarbons. It is understood that aromatic and light paraffin production is promoted by those zeolite catalysts having a high concentration of Bronsted acid reaction sites. Accordingly, an important criterion is selecting and maintaining catalyst inventory to provide either fresh catalyst having acid activity or by controlling catalyst deactivation and regeneration rates to provide an average alpha value of about 1 to 100.

Reaction temperatures and contact time are also significant factors in determining the reaction severity, and the process parameters are followed to give a substantially steady state condition wherein the reaction severity index (R.I.) is maintained within the limits which yield a desired weight ratio of alkane to alkene produced in the reaction zone. This index may vary from about 0.1 to 7:1, in the substantial absence of $C_3+$ alkanes; but, it is preferred to operate the steady state fluidized bed unit to hold the R.I. at about 0.2 to 5:1. While reaction severity is advantageously determined by the weight ratio of propane:propene in the gaseous phase, it may also be measured by the analogous ratios of butanes:butenes, pentanes:pentenes (R.I.5), or the average of total reactor effluent alkanes:alkenes in the $C_3$-$C_5$ range. Accordingly, the product C5 ratio may be a preferred measure of reaction severity conditions, especially with mixed aliphatic feedstock containing $C_3$-$C_4$ alkanes.

This technique is particularly useful for operation with a fluidized catalytic cracking (FCC) unit to increase overall production of liquid product in fuel gas limited petroleum refineries. Light olefins and some of the light paraffins, such as those in FCC light gas, can be converted to valuable $C_5+$ hydrocarbon product in a fluid-bed reactor containing a zeolite catalyst. In addition to $C_2$-$C_4$ olefin upgrading, the load to the refinery fuel gas plant is decreased considerably.

The use of fluidized bed catalysis permits the conversion system to be operated at low pressure drop. Another important advantage is the close temperature control that is made possible by turbulent regime operation, wherein the uniformity of conversion temperature can be maintained within close tolerances, often less than 10° C. Except for a small zone adjacent the bottom gas inlet, the midpoint measurement is representative of the entire bed, due to the thorough mixing achieved.

In a typical process, the olefinic feedstock is converted in a catalytic reactor under oligomerization conditions and moderate pressure (i.e.-400 to 2500 kPa) to produce a predominantly liquid product consisting essentially of $C_5+$ hydrocarbons rich in gasoline-range olefins and essentially free of aromatics.

Referring now to FIG. 2, feed gas rich in lower olefins passes under pressure through conduit 210, with the main flow being directed through the bottom inlet of reactor vessel 220 for distribution through grid plate 222 into the fluidization zone 224. Here the feed gas contacts the turbulent bed of finely divided catalyst particles. Reactor vessel 210 is shown provided with heat exchange tubes 226, which may be arranged as several separate heat exchange tube bundles so that temperature control can be separately exercised over different portions of the fluid catalyst bed. The bottoms of the tubes are spaced above feed distributor grid 222 sufficiently to be free of jet action by the charged feed through the small diameter holes in the grid. Alternatively, reaction heat can be partially or completely removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction can be controlled by adjusting feed temperature in a known manner.

Catalyst outlet means 228 is provided for withdrawing catalyst from above bed 224 and passed for catalyst regeneration in vessel 230 via control valve 229. The partially deactivated catalyst is oxidatively regenerated by controlled contact with air or other regeneration gas at elevated temperature in a fluidized regeneration zone to remove carbonaceous deposits and restore acid acitivity. The catalyst particles are entrained in a lift gas and transported via riser tube 232 to a top portion of vessel 230. Air is distributed at the bottom of the bed to effect fluidization, with oxidation byproducts being carried out of the regeneration zone through cyclone separator 234, which returns any entrained solids to the bed. Flue gas is withdrawn via top conduit 236 for disposal; however, a portion of the flue gas may be recirculated via heat exchanger 238, separator 240, and compressor 242 for return to the vessel with fresh oxidation gas via line 244 and as lift gas for the catalyst in riser 232.

Regenerated catalyst is passed to the main reactor 220 through conduit 46 provided with flow control valve 248. The regenerated catalyst may be lifted to the catalyst bed with pressurized feed gas through catalyst return riser conduit 50. Since the amount of regenerated catalyst passed to the reactor is relatively small, the temperature of the regenerated catalyst does not upset the temperature constraints of the reactor operations in significant amount. A series of sequentially connected cyclone separators 252, 254 are provided with diplegs 252A, 254A to return any entrained catalyst fines to the lower bed. These separators are positioned in an upper portion of the reactor vessel comprising dispersed catalyst phase 224. Filters, such as sintered metal plate filters, can be used alone or conjunction with cyclones.

The product effluent separated from catalyst particles in the cyclone separating system is then withdrawn from the reactor vessel 220 through top gas outlet means 256. The recovered hydrocarbon product comprising $C_5^+$ olefins and/or aromatics, paraffins and naphthenes is thereafter processed as required to provide a desired gasoline or higher boiling product.

Under optimized process conditions the turbulent bed has a superficial vapor velocity of about 0.3 to 2 meters per second (m/sec). At higher velocities entrainment of fine particles may become excessive and beyond about 3 m/sec the entire bed may be transported out of the reaction zone. At lower velocities, the formation of large bubbles or gas voids can be detrimental to conversion. Even fine particles cannot be maintained effectively in a turbulent bed below about 0.1 m/sec.

A convenient measure of turbulent fluidization is the bed density. A typical turbulent bed has an operating density of about 100 to 500 kg/m³, preferrably about 300 to 500 kg/m³, measured at the bottom of the reaction zone, becoming less dense toward the top of the reaction zone, due to pressure drop and particle size differentiation. The weight hourly space velocity and uniform contact provides a close control of contact time between vapor and solid phases, typically about 3 to 15 seconds.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6-2 g/cc, preferably 0.9-1.6 g/cc. The catalyst particles can be in a wide range of particle sizes up to about 250 microns, with an average particle size between about 20 and 100 microns, preferably in the range of 10-150 microns and with the average particle size between 40 and 80 microns. When these solid particles are placed in a fluidized bed where the superficial fluid velocity is 0.3-2, operation in the turbulent regime is obtained. The velocity specified here is for an operation at a total reactor pressure of about 100 to 300 kPa. Those skilled in the art will appreciate that at higher pressures, a lower gas velocity may be employed to ensure operation in the turbulent fluidization regime. The reactor can assume any technically feasible configuration, but several important criteria should be considered.

To demonstrate the invention, the upgrading of FCC light crackate gas is conducted according to the process depicted in FIG. 1 where 0 and 20% of the FCC crackate is bypassed to the conversion reactor. Table I gives the light crackate gas composition in the FCC main column off-gas (A), MOG reactor feed composition (B) with and without slipstream, and sponged MOG process offgas composition (C) with and without slipstream according to this invention. Table II gives the reactor conditions and product gasoline properties.

TABLE I

| Gas Composition, Wt Pct | | | | | |
|---|---|---|---|---|---|
| | | Without Slipstream | | With Slipstream | |
| | A | B | C | B | C |
| H2S | 4.8 | 10.1 | 17.3 | 8.0 | 17.0 |
| H2 | 0.3 | 0.7 | 1.2 | 0.5 | 1.1 |
| C1 | 5.5 | 14.2 | 25.2 | 10.8 | 23.0 |
| C2 | 4.9 | 12.1 | 21.8 | 9.3 | 20.1 |
| C2= | 4.8 | 12.5 | 4.9 | 9.5 | 6.1 |
| C3 | 6.7 | 4.4 | 5.7 | 5.3 | 8.1 |
| C3= | 16.2 | 15.5 | 1.0 | 15.8 | 1.2 |
| IC4 | 10.6 | 3.6 | 2.4 | 6.3 | 4.4 |
| NC4 | 2.8 | 1.1 | 0.4 | 1.7 | 0.7 |
| C4= | 18.1 | 6.3 | 0.8 | 10.9 | 1.1 |
| C5+ | 21.4 | 8.4 | 0.0 | 13.8 | 0.0 |
| N2 + O2 | 3.1 | 8.0 | 14.1 | 6.1 | 12.8 |
| CO2 | 1.0 | 2.7 | 4.7 | 2.0 | 4.3 |
| CO | 0.0 | 0.0 | 0.0 | 0.0 | 0.0 |
| Example Gas Flow Rate (Mlbs/hr) | 200.0 | 77.9 | 44.1 | 102.3 | 48.2 |
| Corresponding C5+ MOG Gasoline recovered, (barrels/day) | | | 1811 | | 3171 |

TABLE II

| Catalyst | HZSM-5 |
|---|---|
| Operating Conditions | |
| WHSV on HC Feed, 1/Hr | 1.00 |
| Reactor Pressure, kPa | 1825 |
| Gas Recycle Ratio, Mol/Mol | 2.0 |
| Avg Reactor Temp, °C. | 376 |
| Reactor 1 Inlet, °C. | 321 |
| T, °C. 75 | |
| Reactor 2 Inlet, °C. | — |
| T. °C. — | |
| Total T 75 | |
| C2= PP at RXT Inlet, KPA | 87.6 |

TABLE II-continued

| | |
|---|---|
| $C_3=$ PP at RXT Inlet, KPA | 33.6 |
| Propane/Propene Ratio | 1.13 |
| Yields on Hydrocarbon, Wt % | |
| C5+ | 73.0 |
| NC4 | 1.7 |
| IC4 | 4.8 |
| C4= | 6.6 |
| C3 | 2.8 |
| C3= | 2.5 |
| C2 | 0.6 |
| C2= | 8.0 |
| C1 | 0.1 |
| Conversion, Wt % | |
| C2 | 83.7 |
| C3= | 94.7 |
| Total Feed Olefin | 89.0 |
| Product Properties | |
| Raw Octane, R + O | 93.1 |
| S.G. at 15.6° C. | 0.734 |

While the invention has been shown by describing preferred embodiments of the process, there is no intent to limit the inventive concept, except as set forth in the following claims.

We claim:

1. A continuous reactor system for upgrading light olefinic crackate gas from hydrocarbon cracking, said light crackate gas containing ethene, propene and other $C_1$–$C_4$ lower aliphatics, comprising:

(a) means for compressing and cooling the light crackate gas to provide a first pressurized ethene-rich vapor stream and a first condensed crackate stream rich in $C_3+$ aliphatics;

(b) deethanizer absorber means for contacting a first portion of said first ethene-rich vapor stream under pressure with a $C_5+$ liquid sorbent stream in a gas-liquid contact column under sorption conditions to selectively absorb a major amount of $C_3+$ components;

(c) means for recovering a second ethene-rich vapor stream from the absorber column;

(d) fluidized bed reactor means for converting said second ethene-rich vapor stream in once-through contact with a fluidized bed of acid medium pore zeolite catalyst solid particles under oligomerization conditions to produce an olefinic hydrocarbon effluent stream rich in $C_5+$ hydrocarbons;

(e) means for cooling and separating the reaction effluent stream to provide a light offgas stream and a condensed liquid hydrocarbon product stream;

(f) first fractionation means for fractionating the liquid hydrocarbon product stream in the absorber column concurrently with sorption of the first ethene-rich vapor stream for recovery of liquid hydrocarbon product with an absorber bottoms liquid stream rich in $C_3+$ components;

(g) second fractionation means for further fractionating the absorber bottoms liquid stream to provide a $C_3$–$C_4$ product and a liquid hydrocarbon fraction consisting essentially of $C_5+$ hydrocarbons;

(h) fluid handling means for recycling at least a portion of the $C_5+$ liquid hydrocarbon fraction to the absorber column as the liquid sorbent stream; and (i) means for bypassing a second portion of said first ethene-rich vapor stream around said absorber means to said reactor means (d) for conversion concurrently with said second ethene-rich vapor stream.

2. A continuous reactor process for upgrading light olefinic crackate gas from hydrocarbon cracking, said light crackate gas containing ethene, propene and other $C_1$–$C_4$ lower aliphatics, comprising:

(a) compressing and cooling a first portion of the light crackate gas to provide a first pressurized ethene-rich vapor stream and a first condensed crackate stream rich in $C_3+$ aliphatics;

(b) contacting said first ethene-rich vapor stream under pressure with a $C_5+$ liquid sorbent stream in a gas-liquid contact absorber column under sorption conditions to selectively absorb a major amount of $C_3+$ components;

(c) recovering a second ethene-rich vapor stream overhead from the absorber column;

(d) converting said second ethene-rich vapor stream in a reaction zone in once-through contact with a fluidized bed of acid medium pore zeolite catalyst solid particles under oligomerization conditions to produce an olefinic hydrocarbon effluent stream rich in $C_5+$ hydrocarbons;

(e) cooling and separating the reaction effluent stream to provide a light offgas stream and a condensed liquid hydrocarbon product stream;

(f) fractionating the condensed liquid hydrocarbon product stream in the absorber column concurrently with sorption of the first ethene-rich vapor stream for recovery of liquid hydrocarbon product with an absorber bottoms liquid stream rich in $C_3+$ components;

(g) further fractionating the absorber bottoms liquid stream to provide a $C_3$–$C_4$ product and a liquid hydrocarbon fraction consisting essentially of $C_5+$ hydrocarbons;

(h) recycling at least a portion of the $C_5+$ hydrocarbon fraction to the absorber column as the liquid sorbent stream; and (i) bypassing a second portion of said light crackate gas around said absorber to step (d) for conversion concurrently with said second ethene-rich vapor stream.

3. The process of claim 2 wherein said second portion of light crackate gas is compressed and mixed with absorber column overhead prior to said reaction zone.

* * * * *